(12) United States Patent
Leese et al.

(10) Patent No.: US 7,202,395 B2
(45) Date of Patent: Apr. 10, 2007

(54) ASSESSMENT METHOD

(75) Inventors: Henry John Leese, York (GB); Francesca Dawn Houghton, York (GB); Peter Gordon Humpherson, York (GB)

(73) Assignee: The University of York (GB)

( * ) Notice: Subject to any disclaimer, the term of this patent is extended or adjusted under 35 U.S.C. 154(b) by 412 days.

(21) Appl. No.: 10/181,387

(22) PCT Filed: Jan. 19, 2001

(86) PCT No.: PCT/GB01/00196

§ 371 (c)(1),
(2), (4) Date: Oct. 21, 2002

(87) PCT Pub. No.: WO01/53518

PCT Pub. Date: Jul. 26, 2001

(65) Prior Publication Data

US 2003/0091977 A1 May 15, 2003

(30) Foreign Application Priority Data

Jan. 19, 2000 (GB) ................................. 0001270.8
Jun. 28, 2000 (GB) ................................. 0015699.2

(51) Int. Cl.
*C12N 15/00* (2006.01)
*C12N 5/00* (2006.01)
*C12N 5/02* (2006.01)
*A61B 17/43* (2006.01)

(52) U.S. Cl. ..................... 800/24; 435/375; 435/377; 600/34

(58) Field of Classification Search .................. 435/4, 435/7.21, 375, 377; 800/24; 600/34
See application file for complete search history.

(56) References Cited

U.S. PATENT DOCUMENTS 5,096,822 A * 3/1992 Rosenkrans et al. ........ 435/388

OTHER PUBLICATIONS

Lee et al, Synergistic effect of alanine and glycine on bovine embryos cultured in a chemically defined medium and amino acid uptake by in vitro-produced bovine morulae and blastocysts, 1996, Biology of Reproduction, 55, 1383-1389.*

Conaghan J, Culture of human preimplantation embryos to the blastocyst stage: a comparison of 3 media, 1998, Int. J. Dev. Biol. vol. 42, pp. 885-893.*

Partridge RJ, Consumption of amino acids by bovine preimplantation embryos, 1996, Reprod. Fertil. Dev., vol. 8, pp. 945-950.*

Orsi NM, Ammonium exposure and pyruvate affect the amino acid metabolism of bovine blastocysts in vitro, 2004, Reproduction, vol. 127, pp. 131-140.*

Lee E, Synergistic effect of alanine and glycine on bovine embryos cultured in a chemically define medium and amino acid uptake by in vitro-produced bovine morulae and blastocysts, 1996, Biology of Reproduction, vol. 55, pp. 1383-1389.*

Baker LM, Experimental design heuristics for scientific discovery: the use of "baseline" and known standard controls, 2000, Int. J. Human-computer Studies, vol. 52, 000-000.*

Barlow DH, A time for consensus and consistency of reporting in clinical studies and the importance of new basic research, 2004, Human Reproduction, vol. 19, pp. 1-2.*

Donnay, I., et al., Embryo Metabolism During the Expansion of the Bovine Blastocyst, *Molecular Reproduction and Development*, vol. 53, pp. 171-178 (1999).

Lamb, V.K., et al., Uptake of a mixture of amino acids by mouse blastocysts, *Journal of Reproduction and Fertility*, vol. 102, pp. 169-175 (1994).

Abstract, Houghton, F.D., et al., Amino acid utilization by the human preimplantation embryo, *Journal of Reproduction and Fertility Abstract Series*, vol. 25, p. 74 (Jul. 2000).

Donnay, Isabelle, et al., Can embryo metabolism be used for selecting bovine embryos before transfer?, *Reproduction Nutrition Development*, vol. 39, No. 5-6, pp. 523-533 (1999).

Patridge, R.J., et al., Consumption of Amino Acids by Bovine Preimplantation Embryos, *Reprod. Fertil. Dev.*, vol. 8, pp. 945-950 (1996).

* cited by examiner

*Primary Examiner*—Ram R. Shukla
*Assistant Examiner*—David A. Montanari
(74) *Attorney, Agent, or Firm*—Myers Bigel Sibley & Sajovec, P.A.

(57) ABSTRACT

A method of assessing the viability of a cell comprises incubating the cell in a culture medium. The culture medium includes a plurality of amino acids and the change in concentration in the medium of at least one amino acid is determined.

22 Claims, 7 Drawing Sheets

ASSESSMENT METHOD

RELATED APPLICATIONS

The present application claims priority from International Application No. PCT/GB01/00196, filed on 19 Jan. 2001, which in turn claims priority from Great Britain application No. 0001270.8, filed on 19 Jan. 2000 and Great Britain application No. 0015699.2, filed on 28 Jun. 2000, the disclosures of which are hereby incorporated herein by reference in their entirety.

FIELD OF THE INVENTION

This invention relates to a method of assessing the viability of a cell.

BACKGROUND OF THE INVENTION

Amino acids have been shown to improve the development of pre-implantation embryos in vitro in a variety of species, such as the mouse (Gardner and Lane 1993), rat (Zhang and Armstrong 1990; Miyoshi et al. 1995), sheep (Gardner et al. 1994) and cow (Takahashi and First 1992; Rosenkrans and First 1994; Keskintepe et al. 1995); Lane and Gardner (1994) reported that Eagle's essential amino acids increased the inner cell mass (ICM) cell numbers in murine embryos cultured from the zygote stage.

Embryos in vivo, derive exogenous amino acids from oviducal and uterine fluids. A total of 20 free amino acids have been detected in bovine oviducal fluid (Stanke et al 1974), and 25 have been detected in bovine uterine fluid (Fahning et al. 1967). Moore and Bondioli (1993) found glycine and alanine to be the two most predominant amino acids in bovine oviducal fluid and that supplementation with these amino acids enhanced bovine embryo development in the presence of oviducal cells. Suh et al. (1995) reported that significantly more bovine zygotes cultured in CR2 medium with glycine reached the blastocyst stage. Rieger and Loskutoff (1994) have shown that glutamine and glycine are consumed by denuded bovine oocytes, and that glutamine is taken up during early pre-implantation development (Rieger et al. 1992).

Although studies in this area have concentrated on administering single or pairs of radiolabelled amino acids, embryos within the female tract will be exposed to a mixture of amino acids (Leese 1988). Lamb and Leese (1994) measured the consumption of a physiological mixture of 20 amino acids by murine blastocysts, and found that 9 were depleted significantly.

The fate of amino acids in bovine embryos has been investigated by Frei et al. (1989) who measured the rate of incorporation of radiolabelled methionine into protein. They found a quantitative decrease in the rate of protein synthesis between the zygote and 8-cell stage, followed by a progressive increase from this point to the blastocyst stage. The quantitative increase in amino acid utilisation observed around these stages of development could be related to the initiation of transcription of the bovine embryonic genome which occurs at the 8-16-cell stage of development (Telford et al. 1990).

Amino acids have also been shown to improve the development of bovine zygotes fertilised in vitro to morulae and blastocysts and to increase total cell numbers at the blastocyst stage (Takahashi and First 1992; Rosenkrans and First 1994; Keskintepe et al. 1995). It is not clear how exogenously-administered amino acids assist embryo development in vitro; some, such as glutamine, may act as energy sources (Rieger and Guay 1988; Rieger 1992), others may increase the pool size of endogenous amino acids and thereby stimulate de novo protein synthesis (Zhang and Armstrong 1990). Van Winkle and Dickinson (1995) have shown that there are significant differences between the amino acid content of murine embryos that develop in vitro and those that develop in vivo.

Partridge and Leese (1996) investigated bovine embryos which had been cultured with 19 amino acids at concentrations routinely used to supplement the medium synthetic oviduct fluid (SOF; Tervit et al. 1972). Groups of embryos fertilised in vitro from the putative zygote stage to the blastocyst stage, and blastocysts freshly flushed from the uterus on Day 7 after fertilisation (derived in vivo) were studied. Depletion rates for 17 of the amino acids were measured over a 12-h period with individual amino acids detected by high performance liquid chromatography (HPLC) following fluorimetric derivatisation.

Partridge and Leese (1996) found glutamine depletion at the putative zygote stage ($0.76 \pm 0.05$ pmol zygote$^{-1}$ h$^{-1}$) and at the 4-cell stage ($0.94 \pm 0.1$ pmol embryo$^{-1}$ h$^{-1}$). However, a greater depletion of glutamine was not observed at the blastocyst stage, in contrast to the results of Rieger et al. (1992) who measured the uptake of radiolabelled glutamine given as a single amino acid substrate in B2 medium by bovine embryos.

With regard to amino acid depletion, a most intriguing result of Partridge and Leese (1996) was the depletion of threonine in significant amounts at all stages of development in vitro as well as by the blastocyst derived in vitro. The fate of threonine is unknown, but it could act as an energy substrate, by entering the Krebs cycle as acetyl-Coenzyme A (CoA) or succinyl-CoA.

Alanine was produced in significant amounts by all stages of embryos produced in vitro and by embryos derived in vivo. Van Winkle and Dickinson (1995) hypothesised that alanine could act as a route for embryos to sequester waste nitrogen since very high concentrations were found in murine blastocysts grown in vitro. In addition, Gardner and Lane (1993) have shown that ammonia toxicity is a potential problem for mouse embryos grown in vitro. The large increase in external alanine concentration observed during the culture of bovine embryos produced in vitro and derived in vivo in the present study leads us to suggest that alanine may indeed be formed by the embryo to prevent the build-up of toxic ammonium ions.

The inclusion of amino acids in human pre-implantation culture medium has become more prevalent since the advent of blastocyst transfer and the requirement for increased embryo development beyond the 4- to 8-cell stage.

In spite of this, there is still little knowledge regarding which amino acids are actually utilised by the embryo at various stages of development.

Current methods for in-vitro embryo production include in-vitro fertilisation and intra cytoplasmic sperm injection (ICSI). Embryo production may also follow the techniques of cryopreservation and embryo biopsy.

Understanding the way in which embryos modify an amino acid mixture may provide a clue to understanding why the embryo produced in vitro is less robust than its in vivo counterpart. These problems are particularly apparent in human in vitro fertilisation (IVF) programmes whereby the average rate of success in the UK is currently about 17% or 1 in 6.

A typical human IVF programme involves the administration of ovarian egg production and releasing hormones to the woman. These eggs are collected and inseminated with sperm to generate about ten embryos. Up to three (in the UK) of the fertilised embryos will then be transferred back to the woman and if the programme is successful, at least one will implant itself in the womb and continue to develop.

In an effort to reduce hormone administration, eggs may be collected at the earlier stages of oogenesis. Subsequent maturation of the eggs occurs in-vitro. Following insemination of the in-vitro matured eggs, up to three fertilised embryos are then transferred back to the woman for implantation.

The method of intra cytoplasmic sperm injection is now increasingly used for fertilisation. Subsequent to the administration of ovarian egg production and releasing hormones, eggs, surrounded by cumulus cells, are released. The protective layer obscures the egg and must be removed to reveal an egg which is then subjected to a system of visual grading before sperm injection is carried out.

To date there exists no method by which embryos or eggs with increased development potential can be effectively and reliably selected, although glucose consumption and lactate production have been used in the mouse for this purpose. Comparative studies of physiological parameters such as glucose, pyruvate, or oxygen consumption in arresting and healthy embryos or eggs have failed to provide a solution to the problem. Current methods rely on morphological selection whereby embryos and eggs are subjected to a grading system.

Because of the great uncertainty in the determination of the most viable embyros and eggs, the need to transfer more than one embryo back into the mother for implantation after artificial insemination becomes apparent. This procedure compensates for the likelihood that one or more of the embryos may fail to develop and serves to heighten the limited chances of success.

Increasing the reliability of the egg or embryo selection will have important ramifications upon the IVF programme as a whole whereby the most viable embryo can be selected and transferred for subsequent implantation. The transfer of a single viable embryo guards against the possibility of multiple births which carries the risk of premature birth and perinatal problems.

It should be understood that any test does not need to be 100% accurate or reliable but should simply provide a non invasive method for consistent indication as to the viability of a single egg or embryo.

A suitable test should involve a selection period which is as short as possible so that transfer of the embryo and implantation can take place as soon as possible after in vitro fertilisation. This minimises any risks which might be associated with prolonged exposure of the developing embryo to the artificial culture conditions. A shorter selection period is also beneficial from an economic point of view because the costs of an otherwise labour and resource intensive operation can be minimised.

Considerable research interest is also focused on the generation of embryos by nuclear transfer (NT). Such embryos are made by injecting a nucleus from a donor cell (karyoplast) into an enucleated egg (ooplast) and then using an electric pulse to trigger embryo development. A variety of karyoplasts have been used for nuclear transfer including stem cells, which are derived from the inner cell mass of the blastocyst and which are the precursor cells for all tisssues of the body. However, embryo-derived stem cells (ES cells) have only been conclusively isolated from the mouse and the human and there is an intensive search for methods to produce them in other species including the domestic species. In the case of 'Dolly' the karyoplast was a somatic (adult) mammary gland cell.

The generation of embryos by nuclear transfer, especially from stem cells, is the preferred route towards the production of transgenic animals and for cell 'therapeutic cloning'—the production of new cells and tissues to replace those which have become diseased or ceased to function properly. However, current methods for the production and identification of karyoplasts, stem cells, stem cell precursors and viable nuclear transfer embryos are laborious and time consuming.

There is a need for a biochemical marker(s) which would simplify the identification of a cell such as a gamete (which may be at any stage of development), an embryo (which may be made by nuclear transfer), a karyoplast, a putative stem cell population, a stem cell precursor population or a stem cell population.

As used herein the term 'egg' refers to an egg at any stage of oogenesis and includes in-vitro matured eggs.

STATEMENTS OF THE INVENTION

According to the present invention there is provided a method of assessing the viability of a cell comprising incubating the cell in a culture medium including a plurality of amino acids and determining the change in concentration in the medium of at least one amino acid.

The term cell is used in its broadest sense and refers to a gamete (which may be at any stage of development), an embryo (which may be made by nuclear transfer), a karyoplast, a putative stem cell population, a stem cell precursor population or a stem cell population.

The term viability is used in its broadest sense to encompass, amongst other things, the development of an embryo to the blastocyst stage, successful implantation of an embryo and pre-implantation screening methods.

Preferably the method of the present invention further comprises the steps of selecting the cell if the change meets a predetermined criterion.

Preferably an embryo which is selected for further development is introduced into the uterine tract of an organism and implants in the uterine wall. An egg which is selected for further development is fertilised to produce an embryo which is introduced into the uterine tract of an organism and implants in the uterine wall. In one embodiment of the invention the egg is an in-vitro matured egg. A karyoplast, putative stem cell population, stem cell precursor population, stem cell population or embryo made by nuclear transfer which is selected for further development may be used in the production of a transgenic organism with desirable qualities such as disease resistance, high lean mass and capacity to produce human medical products in its milk.

Preferably the culture medium comprises Earle's Balanced Salt Solution (EBSS) supplemented with glucose, L-lactate, pyruvate and a physiological mixture of amino acids.

Preferably the concentrations of glucose, L-lactate and pyruvate range from 0.5 mM to 1.5 mM, 4 mM to 6 mM and 0.37 mM to 0.57 mM respectively. More preferably the concentrations of glucose, L-lactate and pyruvate are 1 mM, 5 mM, and 0.47 mM.

Preferably an embryo (which may be made by nuclear transfer), egg, karyoplast, putative stem cell population, stem cell precursor population or stem cell population is cultured in approximately 4 µl drops of culture medium. The concentration of amino acids in the spent medium is measured using HPLC, preferably followed by derivatisation with o-phthaldialdehyde, and an amino acid consumption and production profile is generated.

In order to achieve accurate dilution of the microliter samples for use in HPLC, an internal standard is introduced into the medium. Preferably the internal standard is D-alpha-aminobutyric acid.

The present invention also provides for a diagnostic kit including means for incubating a cell in a culture medium and means for determining the change in concentration in the medium of at least one amino acid. The diagnostic kit generates an amino acid profile showing consumption or production of amino acids in the culture medium in which the test cell is incubated. Preferably the diagnostic kit allows for a comparison of the amino acid profile of the incubated cell with predetermined 'finger-print' amino acid profiles for arresting and healthy cells of a particular organism of study. Accordingly, the amino acid profiles are used as a selection marker in the selection of the most viable cells.

The amino acid consumption or production profile can be used to verify the presence of a putative stem cell population, stem cell precursor population or stem cell population which will be characterised by a particular amino acid profile. The putative stem cell population, stem cell precursor population or stem cell population can then be used in genetic manipulation to produce transgenic organisms. The method of the present invention represents an enormous advantage over current techniques by providing a simple biochemical marker for stem cell identification and selection.

Using the method of the present invention, selection of a cell is preferably achieved in 24 hours or less after transfer of the cell into the culture medium. More preferably selection is achieved in 10 hours or less after transfer of the cell into the culture medium. Most preferably selection is achieved in 6 hours or less.

In one embodiment of the invention the 'fingerprint' amino acid profile is used as a whole as a selection marker to select a viable cell for a particular species. In a separate embodiment of the invention, selection of the most viable cell is based upon a smaller group of amino acids, typically comprising one to five amino acids, whose consumption or production profile is indicative of a healthy cell for that species.

The method of the invention may be used for a variety of organisms including humans, cows, pigs, sheep and any other domestic animals. The amino acids used for a selection marker may include any or a plurality of amino acids. In one embodiment of the invention, the method is used for humans and the amino acids used for a selection marker include any or a combination of the amino acids alanine, arginine, aspartic acid, glutamic acid, glutamine, glycine, leucine, lysine, tryptohan, valine. In one embodiment of the invention, the amino acid used for a selection marker is alanine.

DETAILED DESCRIPTION OF THE INVENTION

The present invention will now be described by way of example only and with reference to the accompanying drawings wherein.

Figure 1:
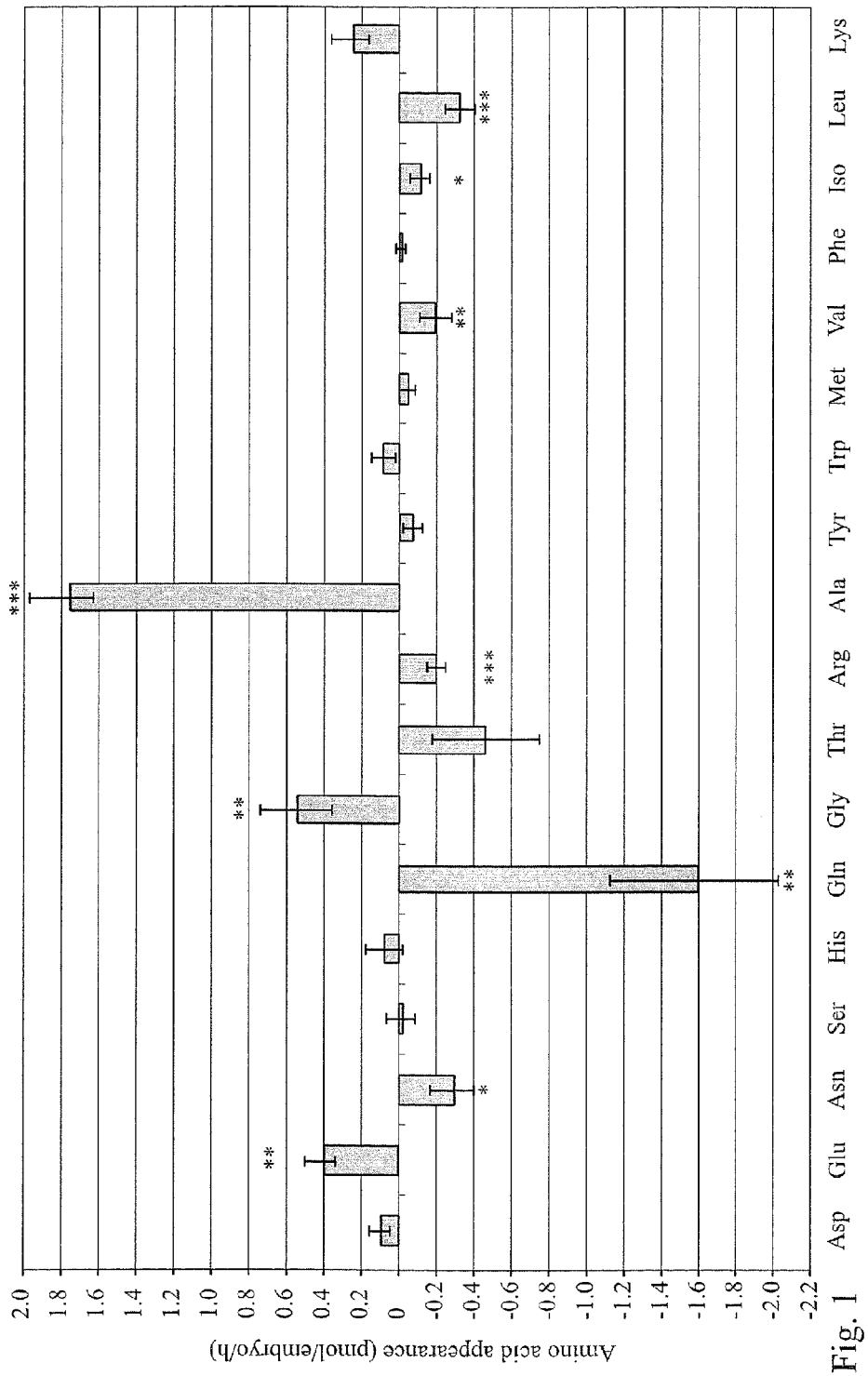
FIG. 1 shows the mean amino acid consumption or production profile (pmol/embryo/h) for 27 human embryos which arrested development at the 8-cell stage. Amino acids which were significantly consumed or produced are marked with an asterix.
Figure 2:
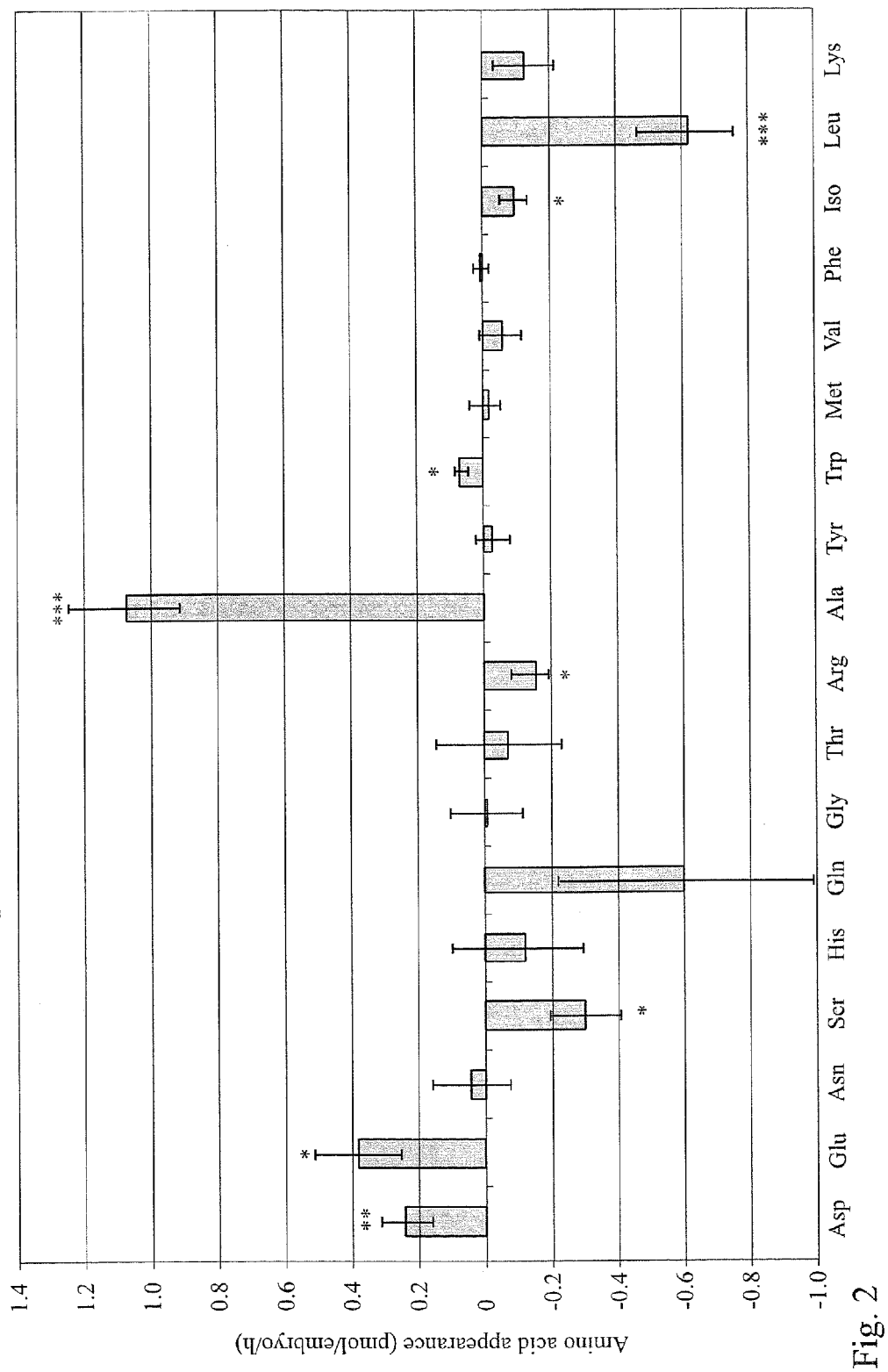
FIG. 2 shows the mean amino acid consumption or production profile (pmol/embryo/h) for 22 human embryos at the compacting 8-cell stage which developed to the blastocyst stage. Amino acids which were significantly consumed or produced are marked with an asterix.
Figure 3:
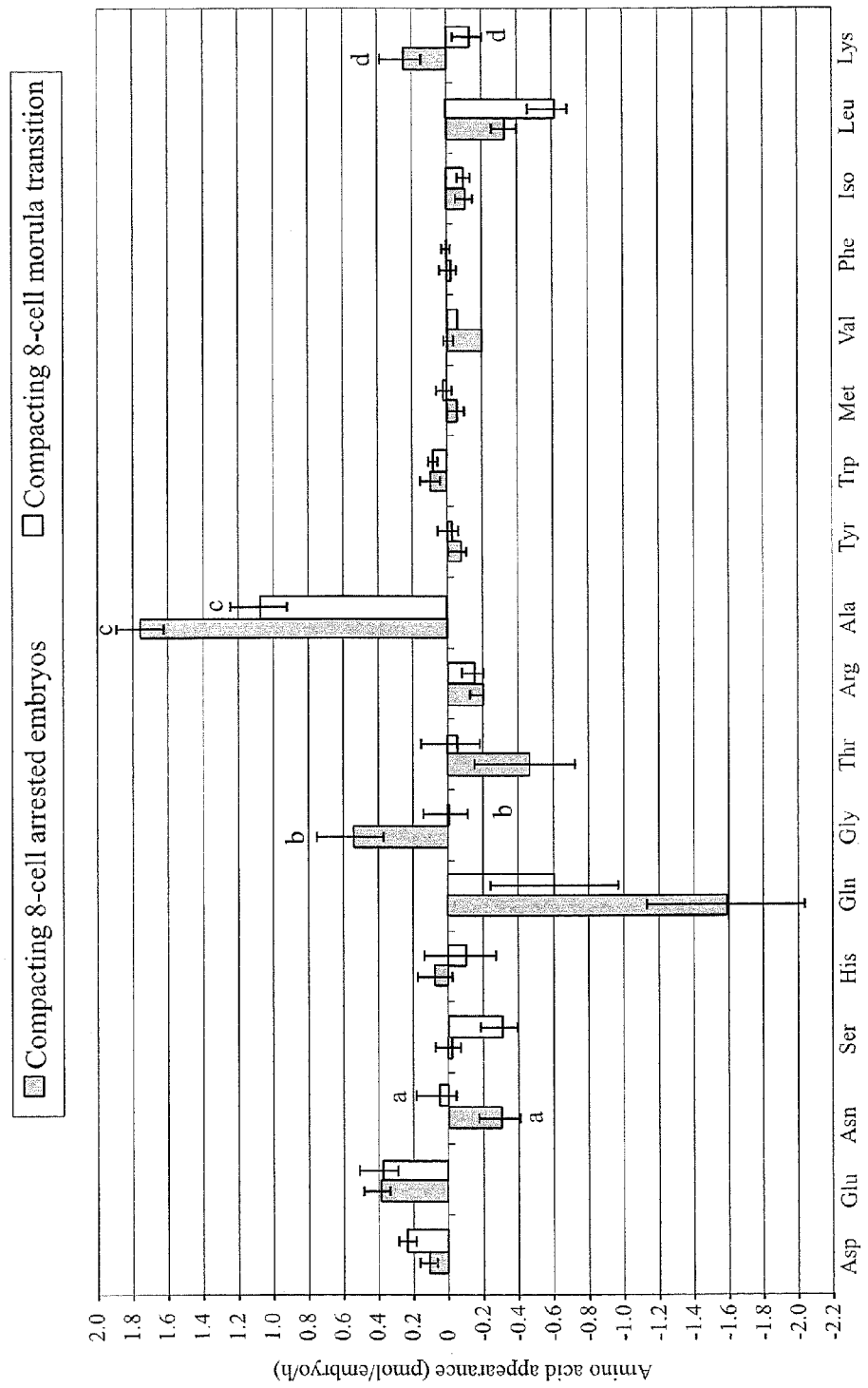

FIG. 3 is a superimposition of the data from FIGS. 1 and 2 and compares the amino acid consumption or production (pmol/embryo/h) for human embryos which arrested development at the 8-cell stage (shaded bars) and human embryos which developed to the blastocyst stage (unshaded bars). T-tests were used to compare the consumption or production data for each amino acid for each group of arresting and developing embryos. A p-value of less than 0.05 was considered significant. Data for the amino acids marked with the superscript a, b, c or d (alanine, asparagine, glycine and lysine respectively) are significantly different for the two sets of tests.

Figure 4:
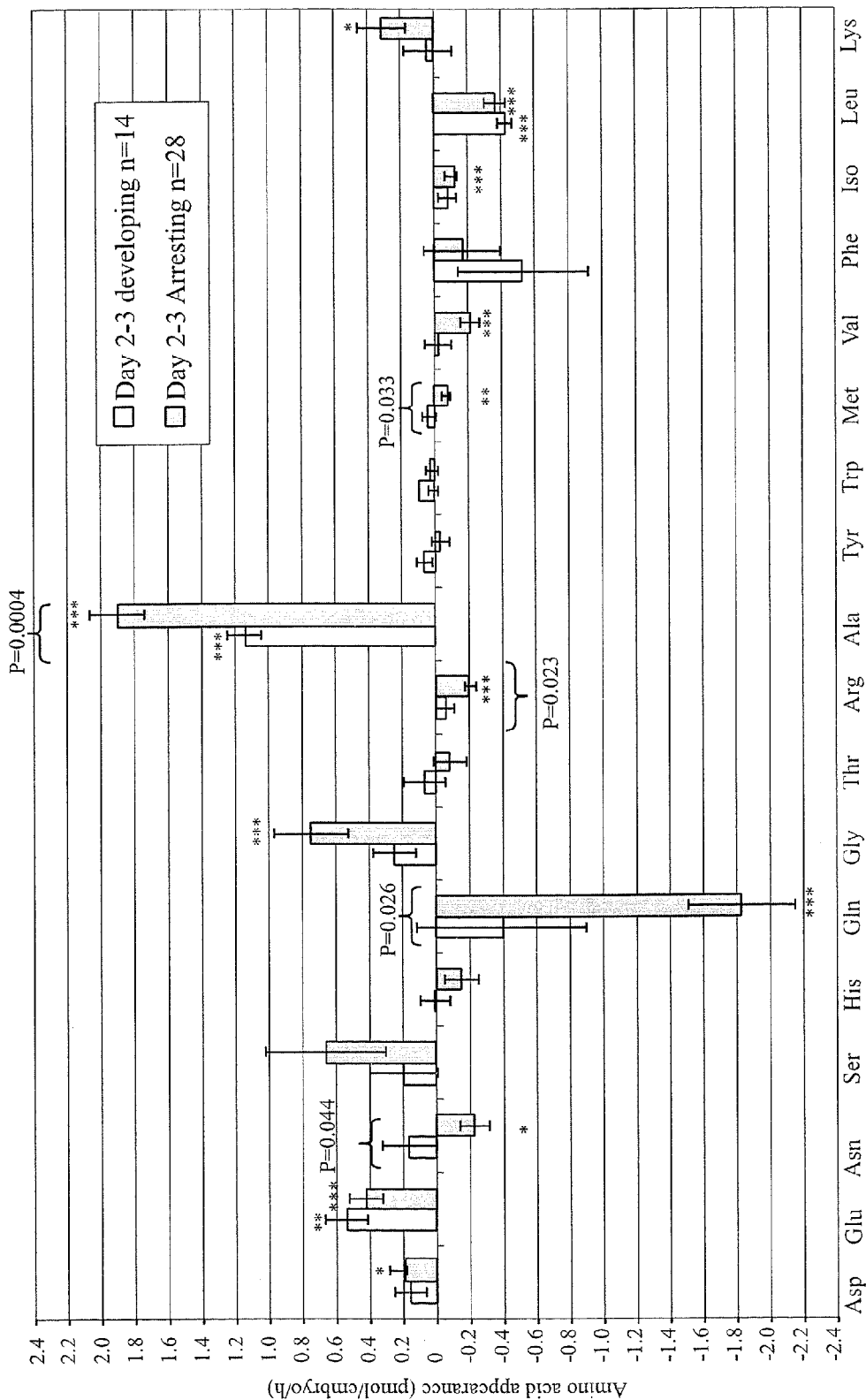

FIG. 4 is a superimposition of data to compare amino acid consumption or production (pmol/embryo/h) for human embryos from day 2 to day 3 post fertilisation which arrested development at the 8-cell stage (shaded bars) and human embryos from day 2 to day 3 post fertilisation which developed to the blastocyst stage (unshaded bars).

Figure 5:
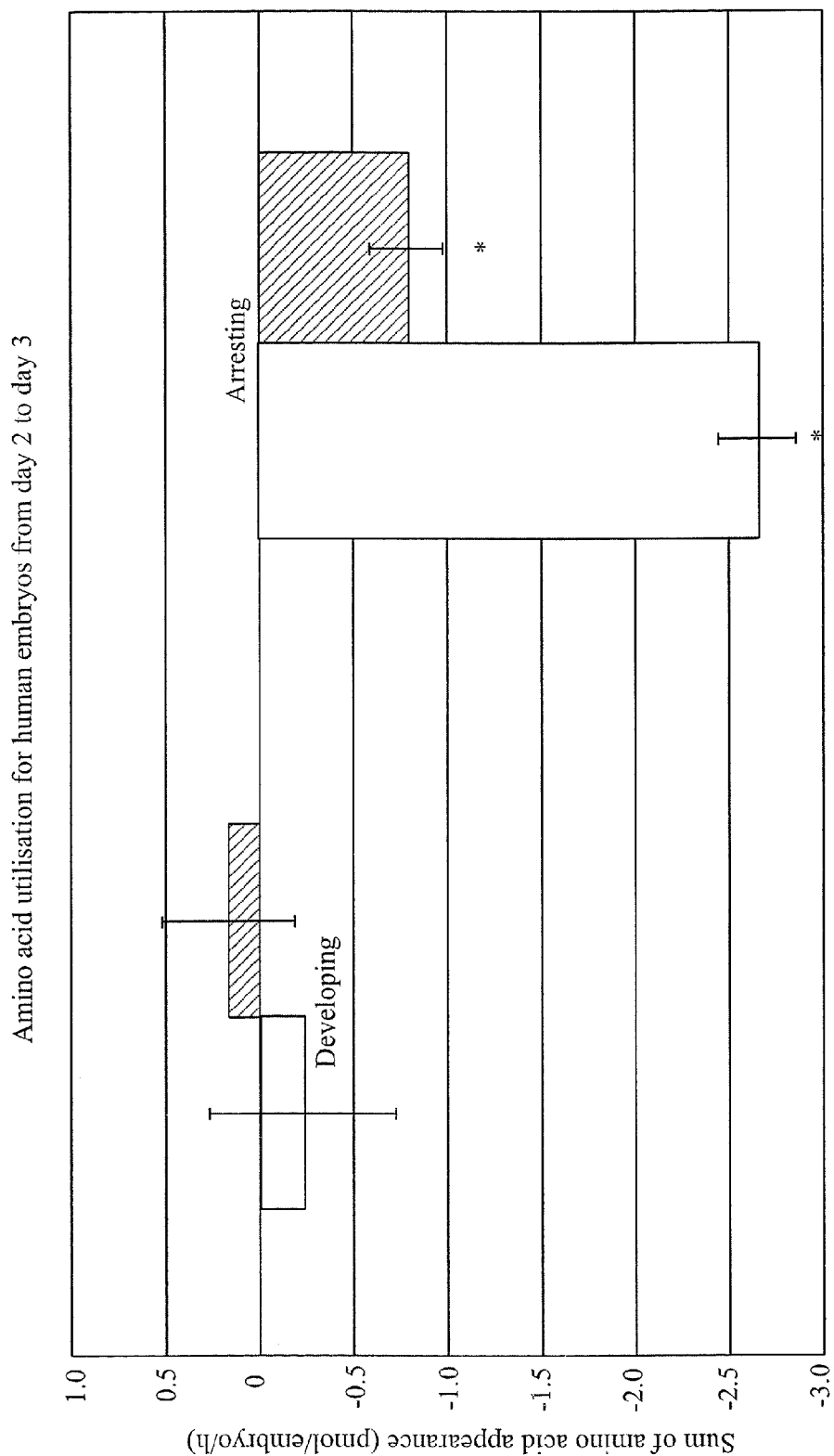

FIG. 5 shows the sum of utilisation of five amino acids in developing and arresting human embryos from day 2 to day 3 post fertilisation.

Figure 6:
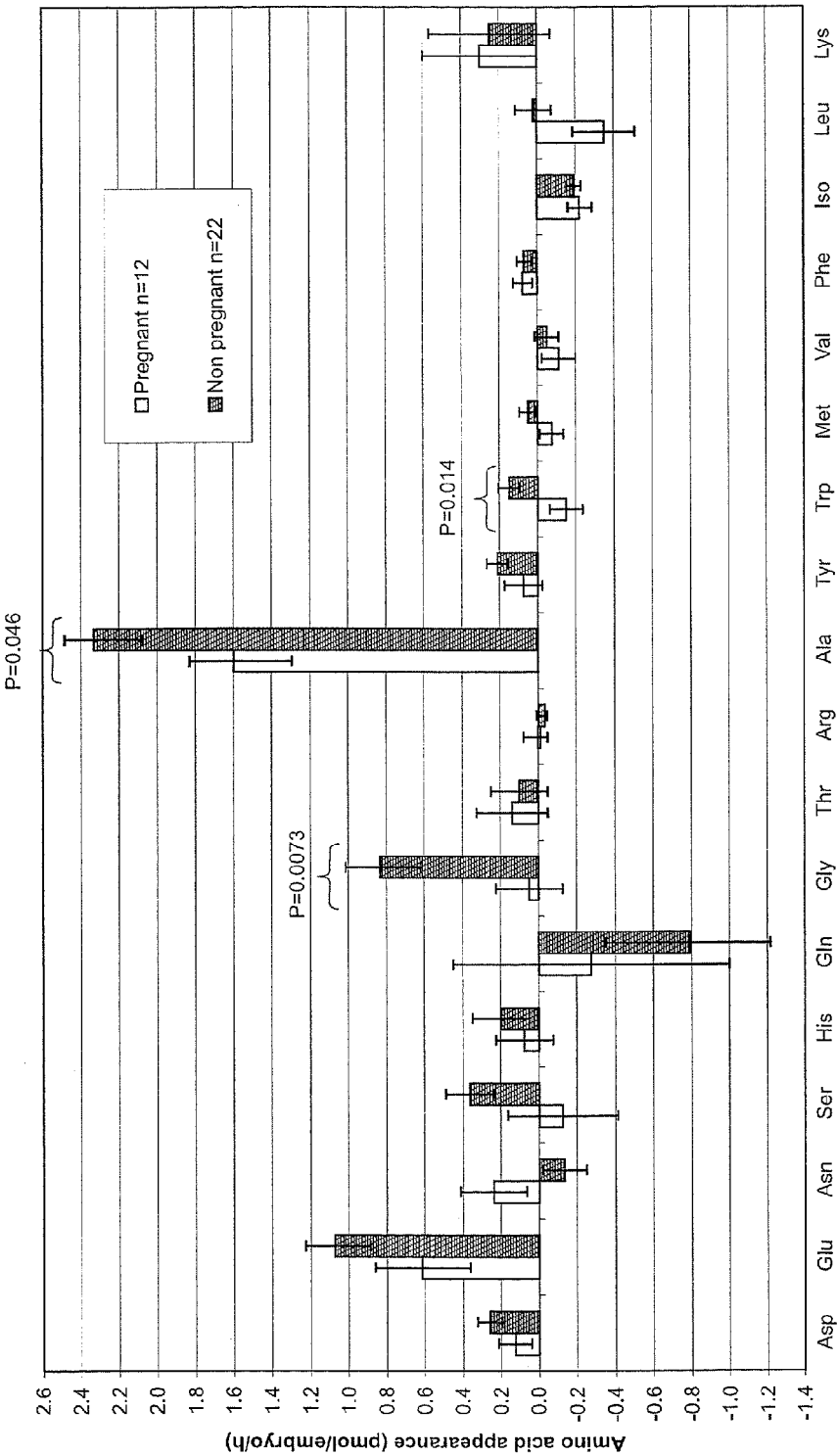

FIG. 6 is a superimposition of data to compare amino acid consumption or production (pmol/embryo/h) for ICSI embryos that resulted in pregnancy (unshaded bars) and that failed to result in pregnancy (shaded bars) from day 1 to day 2 of development.

Figure 7:
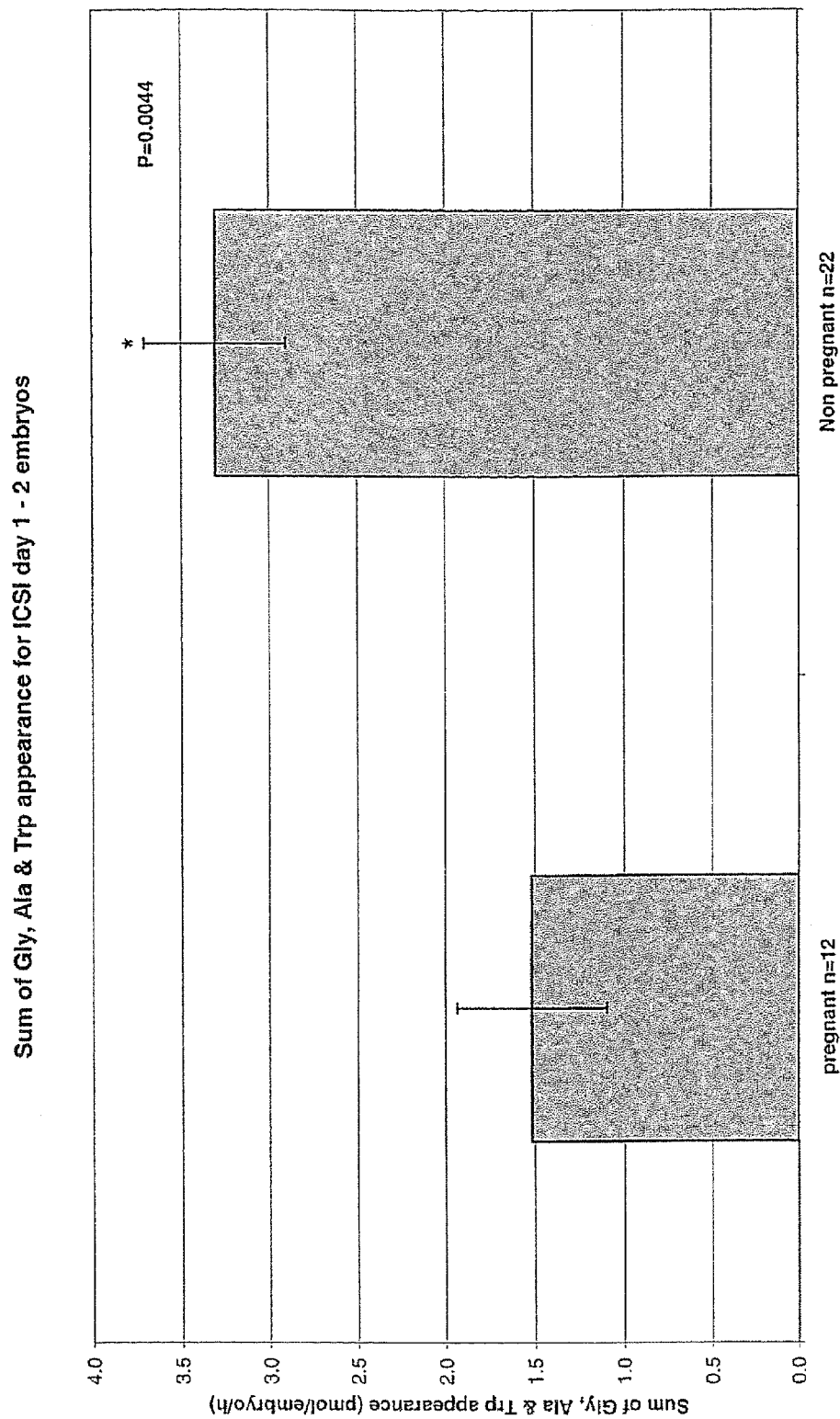

FIG. 7 shows the sum of Gly, Ala and Trp appearance for ICSI embryos that resulted and failed to result in pregnancy, from day 1 to day 2 of development.

In initial experiments, spare in vitro fertilised human embryos were individually placed in 4 µl drops of culture medium until they reached the blastocyst stage. Embryos were cultured individually to mimic the conditions which are encountered by an embryo developing in vivo. The culture medium comprised 4 µl drops of EBSS supplemented with 1 mM glucose, 5 mM L-lactate, 0.47 mM pyruvate and a physiological mixture of 20 amino acids. The individual concentrations of the amino acids were in the range 0.005 mM to 1.0 mM.

During incubation, the concentration of 18 amino acids in the spent medium was simultaneously measured using high performance liquid chromatography (HPLC) following derivatisation with o-phthaldialdehyde. The results were used to compile amino acid consumption and production profiles as illustrated in FIGS. 1 to 3.

In order to achieve accurate dilution of microliter samples for use in HPLC, an internal standard in the form of the non metabolisable amino acid; D-alpha-aminobutyric acid, was introduced into the medium at a concentration of 1 in 49 parts per volume. This internal standard allowed the minute differences that occur in resting embryos, and which would otherwise be lost in the 'back-ground noise' to be picked up. The HPLC peak attributable to the marker can be easily distinguished and was used to calculate the correct dilution.

As shown in FIG. 2, the only amino acids that were significantly depleted from the medium during the compacting 8-cell to the morula stage were serine, arginine, isoleucine and leucine. Alanine, aspartate, glutamate and tryptophan were significantly produced. Alanine appearance increased from 10.87±1.61 pmol/embryo/h for embryos cultured between the compacting 8-cell to the morula stage compared to 13.90±1.23 pmol/embryo/h for embryos cultured from the morula to blastocyst stage.

Embryos that arrested at the compacting 8-cell stage produced significantly more alanine (17.72±1.44 pmol/embryo/h; p=0.0028) than developing embryos of the same stage (FIGS. 1 to 3). Glutamate was also significantly produced over the morula to blastocyst transition.

Although it is known that an embryo will cause changes to the amino acid concentration of a culture medium in which it is incubated, the significant differences in the changes brought about by healthy and arresting embryos have previously gone unnoticed. It should be understood that the results of the embryo experiments are highly indicative of those which would be expected for an egg, karyoplast, stem cell, stem cell precursor or embryo made by nuclear transfer subjected to the same incubation conditions. Accordingly, the change in concentration of at least one amino acid in the culture medium can be used to give an indication as to the viability of an embryo, egg, karyoplast, stem cell, stem cell precursor or embryo made by nuclear transfer. This represents a major advance in the selection of embryos or eggs for subsequent implantation and the selection of karyoplasts, stem cells, stem cell precursors or embryos made by nuclear transfer for genetic manipulation.

The increased production of alanine by arresting embryos for example is surprising and counter-intuitive. If alanine is used as a route to sequester waste nitrogen and is formed by the embryo to prevent the build-up of toxic ammonium ions, it might be expected that the healthiest embryos would be most metabolically active and produce higher quantities of alanine as compared with arresting embryos. Surprisingly, the results show that healthiest embryos are metabolically 'quieter' and that embryos which fail to develop turnover comparatively more protein with the amino groups being exported into the culture medium as alanine.

The results indicate that the human pre-implantation embryo is able to use amino acids selectively at different stages of development and that the appearance of alanine in the medium may be used as a potential marker of the viability of an embryo, egg, karyoplast, stem cell, stem cell precursor or embryo made by nuclear transfer.

The method of the present invention could be used in pre-implantation screening for diseases such as phenylketonuria (PKU), cystic fibrosis and other such genetic or chromosomal abnormalities.

All babies in the UK are currently tested for PKU a few days after birth by measuring the phenylalanine level in the blood using chromatography or a bacterial growth test. It is likely that those embryos or eggs which are predestined to PKU are characterised by a different amino acid profile compared with that produced by a healthy embryo or egg. Accordingly the method of the present invention carries huge potential for future genetic screening programs.

The method of the present invention may also have immense value in sex determination whereby embryos of different sex may be characterised by a certain amino acid profile.

It should be understood that the method of the invention has wide reaching applications and is not limited to the use of a human embryo, egg, karyoplast, stem cell, stem cell precursor or embryo made by nuclear transfer. A typical method in cattle breeding is the administration of egg inducing hormones to a cow of high genetic merit followed by natural insemination leading to the production of about 6 to 8 embryos in the uterus of the animal. The embryos are then 'flushed' from the cow and transferred singly to lower grade animals for subsequent development. Due to the risks of improper flushing, this technique is unethical for use in man.

Alternatively, egg production in a valuable cow is hormonally induced and following retrieval (ovum pick-up), the eggs are artificially inseminated using high quality sperm and cultured to the blastocyst stage before subsequent transferral back to a recipient. Cattle embryos may also be generated from oocytes derived from abattoir ovaries.

Such cattle breeding programmes are of multi-national concern and any selection method by which the most viable eggs or embryos for transfer can be selected represents a major industrial advance.

Other animals to which this technology may be applicable include sheep, pigs, all domestic animals and rare and threatened species. The cloning technology used in production of 'Dolly' was met by low success rates with 276 previously failed attempts. The 'Dolly' programme also involved considerable expenditure of research effort in the attempt to generate appropriate sheep cells to produce transgenic animals.

The method of the present invention now provides a rational approach to the selection of the most viable cell for use in subsequent embryo or egg transfer and to the selection of karyoplasts, putative stem cell populations, stem cell precursor populations, stem cell populations and embryos made by nuclear transfer. It represents a major advance in farm animal improvement techniques which involve micromanipulation, nuclear transfer and the addition of genetic constructs.

It should be understood that the amino acid profile for a cell of a particular organism may be highly discrete; differing in detail as to which particular amino acids are consumed and produced and also which particular amino acids are consumed and produced in arresting and developing cells when compared with that profile generated for a cell of a different organism. Although the results suggest that alanine may be used as a potential marker for the viability of human cells, further investigations may reveal that other amino acids are more suitable markers for other species. Indeed, further investigation of the human embryo reveal that additional amino acids besides alanine are also suitable for use as a selection marker.

The initial study was based upon human embryos from day 3 to day 4 post insemination. As shown in FIG. 3, lysine is produced in arresting embryos and consumed in healthy embryos. This might have selection potential. Similarly the results for asparagine and glycine are significant. It was suspected that as more tests are carried out, the significant differences between amino acid consumption and production for healthy and arresting embryos may increase.

Studies were extended to human embryos from day 2 to day 3 post insemination. Earlier assessment was considered advantageous since it is preferable to minimise the exposure of the developing embryo to artificial culture conditions as far as possible. The results of these experiments are illustrated in FIGS. 4 and 5.

Subsequent studies involved the collection of pregnancy data. ICSI embryos were analysed from day 1 to day 2 of development, before subsequent transfer into patients. The choice of ICSI embryos versus IVF embryos was due to the fact that the cumulus of an ICSI embryo has been removed, thus facilitating assessment. Now the focus was not so much the identification of healthy, pre-implantation embryos but whether the embryo would implant within the mother (i.e., a move towards the clinical side).

ICSI embryos were incubated in culture medium comprising EBSS supplemented with 1 mM glucose, 5 mM L-lactate, 0.47 mM pyruvate and a physiological mixture of 20 amino acids. The individual concentrations of the amino acids were in the range 0.005 mM to 1.0 mM.

The results from this line of the investigation were particularly encouraging and provide corroborative evidence for the efficacy of the assessment method.

The method of the present invention allows for the generation of 'finger-print' amino acid profiles which are characteristic for a particular species and which can be used in selecting the most viable cell for that species.

Because it is not known which embryo will develop to term, typically two or three embryos are transferred back into the mother after artificial insemination. The method of the present invention reduces the likely of multiple pregnancy by providing a biochemical test for the selection of a single embryo. This is considerably more accurate than morphological selection methods.

The invention claimed is:

1. A method of assessing the ability of a mammalian pre-implantation embryo to develop to a blastocyst stage and/or be successfully implanted, said method comprising:
   (i) incubating the mammalian pre-implantation embryo in a culture medium comprising a plurality of amino acids;
   (ii) determining an increase or decrease in concentration of at least one amino acid in the culture medium to determine amino acid turnover, wherein said at least one amino acid is selected from the group consisting of alanine, arginine, glutamine, glycine, leucine, methionine, asparagine and serine, as compared to pre-culture medium;
   (iii) selecting a pre-implantation embryo in the culture medium of step ii;
   wherein said culture medium has a higher or lower concentration of at least one of said at least one amino acids, and wherein the pre-implantation embryo of step (iii) has an increased possibility of development to the blastocyst stage and/or successful implantation.

2. The method according to claim 1 further comprising the step of selecting said mammalian pre-implantation embryo for further development to the blastocyst stage and/or implantation.

3. The method according to claim 1 wherein the culture medium comprises Earle's Balanced Salt solution supplemented with glucose, L-lactate, pyruvate and a physiological mixture of amino acids.

4. The method according to claim 3 wherein the concentrations of glucose, L-lactate, and pyruvate range from 0.5 mM to 1.5 mM, 4 mM to 6 mM and 0.37 mM to 0.57 mM respectively and the concentrations of individual amino acids in the culture medium range from 0.005 mM to 1.0 mM.

5. The method according to claim 4 wherein the concentrations of glucose, L-lactate and pyruvate are 1 mM, 5 mM, and 0.47 mM respectively.

6. The method according to claim 1 further comprising determining the concentration of amino acids in the spent medium by HPLC followed by derivatisation with o-phthaldialdehyde.

7. The method according to claim 6 wherein an internal standard is introduced into the sample medium in order to achieve accurate dilution of the microliter samples for use in HPLC.

8. The method according to claim 7 wherein the internal standard is D-alpha-aminobutyric acid.

9. The method according to claim 1 wherein the ability of the mammalian pre-implantation embryo to develop to the blastocyst stage and/or be successfully implanted is achieved in 24 hours or less after transfer of the mammalian pre-implantation embryo into the culture medium.

10. The method according to claim 9 wherein the ability of the mammalian pre-implantation embryo to develop to the blastocyst stage and/or be successfully implanted is achieved in 10 hours or less after transfer of the mammalian pre-implantation embryo into the culture medium.

11. The method according to claim 10 wherein the ability of the mammalian pre-implantation embryo to develop to the blastocyst stage and/or be successfully implanted is achieved in 6 hours or less after transfer of the mammalian pre-implantation embryo into the culture medium.

12. The method according to claim 1 wherein the mammalian pre-implantation embryo is derived from a mammal selected from the group consisting of humans, cows, pigs, and sheep.

13. The method according to claim 12 wherein the mammalian pre-implantation embryo is derived from a human.

14. The method according to claim 13 wherein the at least one amino acid is alanine, cysteine, aspartic acid, glutamic acid, phenylalanine, glycine, histidine, isoleucine, lysine, leucine, methionine, asparagine, proline, glutamine, arginine, seine, threonine, valine, tryptophan, or tyrosine.

15. The method according to claim 14 wherein the at least one amino acid is at least one of asparagine, glycine, arginine or leucine.

16. The method according to claim 1 wherein the method is used to assess the ability of the mammalian pre-implantation embryo to implant and give rise to a clinical pregnancy.

17. The method according to claim 16 wherein the mammalian pre-implantation embryo is assessed from day 1 up to day 4 of development.

18. The method according to claim 2 further comprising introducing the selected mammalian pre-implantation embryo into the uterine tract of a mammal.

19. The method of claim 1, wherein the mammalian pre-implantation embryo is a mammalian pre-implantation embryo derived from an in-vitro matured egg.

20. The method of claim 1 wherein the mammalian pre-implantation embryo is produced by intra-cytoplasmic sperm injection.

21. The method of claim 12, wherein the mammalian pre-implantation embryo is derived from a cow.

22. The method according to claim 14 wherein the at least one amino acid is at least one of alanine, arginine, glutamine, methionine or asparagine.

* * * * *

UNITED STATES PATENT AND TRADEMARK OFFICE
CERTIFICATE OF CORRECTION

PATENT NO. : 7,202,395 B2 Page 1 of 1
APPLICATION NO. : 10/181387
DATED : April 10, 2007
INVENTOR(S) : Leese et al.

It is certified that error appears in the above-identified patent and that said Letters Patent is hereby corrected as shown below:

On The Title Page
Sec. (75) Inventors: Please correct "Francesca Dawn Houghton, York (GB)"
To read --Franchesca Dawn Houghton, York (GB)--

In The Claims:

Column 10, Claim 7, Line 3: Please correct "microliter"
To read -- microlitre--

Column 10, Claim 14, Line 33: Please correct "seine,"
To read -- serine,--

Column 10, Claim 15, Line 35: Please Add --serine,-- after "glycine,"

Signed and Sealed this

Seventh Day of August, 2007

JON W. DUDAS
*Director of the United States Patent and Trademark Office*